(12) United States Patent
Stone (10) Patent No.: US 6,480,729 B2
(45) Date of Patent: Nov. 12, 2002

(54) METHOD FOR DETERMINING BLOOD CONSTITUENTS

(75) Inventor: Robert T. Stone, Sunnyvale, CA (US)

(73) Assignee: Alexander K. Mills, San Antonio, TX (US)

( * ) Notice: Subject to any disclaimer, the term of this patent is extended or adjusted under 35 U.S.C. 154(b) by 0 days.

(21) Appl. No.: 09/817,667

(22) Filed: Mar. 26, 2001

(65) Prior Publication Data
US 2001/0037058 A1 Nov. 1, 2001

Related U.S. Application Data
(60) Provisional application No. 60/200,332, filed on Apr. 28, 2000.

(51) Int. Cl.$^7$ .............................................. A61B 5/00
(52) U.S. Cl. ..................... 600/323; 600/334; 600/336; 600/322
(58) Field of Search ..................... 600/309–311, 316, 600/330, 322–324, 334–336; 356/39–41

(56) References Cited

U.S. PATENT DOCUMENTS

| 3,998,550 | A | | 12/1976 | Konishi et al. |
| 4,167,331 | A | | 9/1979 | Nielsen |
| 4,266,554 | A | | 5/1981 | Hamaguri |
| 4,407,290 | A | | 10/1983 | Wilber |
| 4,883,055 | A | | 11/1989 | Merrick |
| 4,934,372 | A | | 6/1990 | Corenman et al. |
| 5,078,136 | A | | 1/1992 | Stone |
| 5,193,543 | A | | 3/1993 | Yelderman |
| 5,490,505 | A | | 2/1996 | Diab et al. |
| 5,575,284 | A | * | 11/1996 | Athan et al. ................. 600/323 |
| 5,755,226 | A | * | 5/1998 | Carim et al. ................. 600/323 |
| 5,784,151 | A | * | 7/1998 | Miller et al. ................... 356/41 |
| 5,827,181 | A | * | 10/1998 | Dias et al. ................... 600/322 |
| 5,860,919 | A | * | 1/1999 | Kiani-Azarbayjany et al. .......................... 600/322 |
| 6,094,592 | A | * | 7/2000 | Yorkey et al. ............... 600/475 |
| 6,222,189 | B1 | * | 4/2001 | Misner et al. ............ 250/341.1 |

FOREIGN PATENT DOCUMENTS

| EP | 0 102 816 A2 | 3/1984 |
| EP | 0 104 771 B1 | 4/1984 |

* cited by examiner

Primary Examiner—Eric F. Winakur
Assistant Examiner—Matthew Kremer
(74) Attorney, Agent, or Firm—Francis Law Group (57) ABSTRACT

A method for determining the blood constituents of a patient comprising coupling an oximeter sensor arrangement to a tissue region of the patient; passing first and second lights through the patient's tissue region for a first period of time while the venous blood in the tissue region has a first volume and for a second period of time while the venous blood in the tissue region has a second volume, the first light being substantially in a red light range and the second light being substantially in an infrared light range; detecting a red light signal and an infrared light signal, the red and infrared signals having at least first and second frequencies; computing a first ratio of the red and infrared signals at the first frequency; computing a second ratio of the red and infrared signals at the second frequency; comparing the first and second ratios to determine a first blood constituent.

27 Claims, 7 Drawing Sheets

METHOD FOR DETERMINING BLOOD CONSTITUENTS

CROSS REFERENCE TO RELATED APPLICATIONS

This application claims benefit under 35 U.S.C. 119 (e) of U.S. Provisional Application No. 60/200,332, filed Apr. 28, 2000.

FIELD OF THE INVENTION

The present invention relates to non-invasive pulse oximetry. More specifically, the present invention relates to a method for detecting the venous blood component in a pulse oximetry signal.

BACKGROUND OF THE INVENTION

Non-invasive photoelectric pulse oximetry for determining blood flow characteristics is well known in the art. Illustrative are the methods and apparatus described in U.S. Pat. Nos. RE 35,122; 5,193,543; 5,448,991; 4,407,290; and 3,704,706.

Pulse oximeters typically measure and display various blood constituents and blood flow characteristics including, but not limited to, blood oxygen saturation of hemoglobin in arterial blood, the volume of individual blood pulsations supplying the flesh and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured.

Two lights having discrete frequencies in the range of ~650–670 nanometers in the red range and ~800–1000 nanometers in the infrared range are typically passed through the tissue. The light is absorbed by the blood in an amount representative of the amount of the blood constituent present in the blood. The amount of transmitted light passed through the tissue will vary in accordance with the changing amount of blood constituent in the tissue and the related light absorption.

The output signal from the pulse oximeter, which is sensitive to the arterial blood flow, contains a component that is waveform representative of the patient's blood gas saturation. This component is referred to as a "plethysmographic wave or waveform" (see curve P in FIG. 1).

A problem generally associated with non-invasive pulse oximeters is that the plethysmograph signal (and the optically derived pulse rate) may be subject to irregular variants in the blood flow including, but not limited to, motion artifacts, that interfere with the detection of the blood constituents. A motion artifact is caused by the patient's muscle movement proximate to the oximeter sensor, for example, the patient's finger, ear or other body part to which the oximeter sensor is attached, and may cause spurious pulses that are similar to pulses caused by arterial blood flow. These spurious pulses, in turn, may cause the oximeter to process the artifact waveform and provide erroneous data. This problem is particularly significant with infants, fetuses, or patients that do not remain still during monitoring.

A further problem is that the plethysmograph signal includes the blood oxygen saturation signals of the venous (i.e., non-pulsating) and arterial (i.e., pulsating) blood. The inability to reliably detect the venous blood component in the optical signal could, and in many instances will, result in erroneous data.

Several signal processing methods (and apparatus) have been employed to reduce the effects of the motion artifact(s) on the measured signal(s) and, hence, derived plethysmograph waveform. Illustrative are the methods and apparatus disclosed in U.S. Pat. Nos. 4,934,372 and 5,490,505.

In Co-pending application Ser. No. 09/815,827, filed Mar. 23, 2001, entitled "Method and Apparatus For Determining Physiological Characteristics", a unique method and apparatus is disclosed that employs an "individualized", substantially noise free plethysmographic waveform as a reference signal. The noted reference is transmitted to a correlation canceler that provides a derived plethysmographic waveform that is substantially representative of the subject's true plethysmographic waveform.

Several methods and apparatus have also been employed to detect the venous blood component in an optical signal. One method relies upon the quantitative measurement in the change in absorbance at each wavelength, as in U.S. Pat. No. 4,407,290 and European patent Nos. EP 0 104 771 A3 and EP 0 102 816 A3. It is also well known that the derivative of the change in absorbance and a peak to peak measurement of the pulsating absorbance component may be used to calculate the oxygen content of arterial blood, as disclosed in U.S. Pat. Nos. 4,407,290 and 4,167,331.

It is further known that a single light detector may be employed. However, when a single light detector is used, the detected light for each wavelength must be separated. This is accomplished by using time separation and synchronous detection, as disclosed in U.S. Pat. Nos. 4,407,290; 4,266,554; and 3,647,299, for example. However, since the light detectors also detect ambient light, some type of ambient light rejection technique is normally employed. One technique is to use four clock states and to allow for the subtraction of ambient light, as disclosed in U.S. Pat. Nos. 4,407,290 and 4,266,544. Another technique is to remove the non-pulsating absorbance component, since ambient light is usually a non-pulsating absorbance frequency, as disclosed in U.S. Pat. Nos. 4,167,331 and 3,998,550.

There are several drawbacks associated with the noted technologies and apparatus. Among the drawbacks are the cost and complexity of the disclosed apparatus.

It is therefore an object of the present invention to provide a cost effective, reliable means of determining the venous blood component in an optical pulse oximeter signal.

SUMMARY OF THE INVENTION

In accordance with the above objects and those that will be mentioned and will become apparent below, the method for determining the blood constituents of a patient in accordance with this invention comprises coupling an oximeter sensor arrangement to a tissue region of the patient; passing first and second lights through the patient's tissue region for a first period of time while the venous blood in the tissue region has a first volume and for a second period of time while the venous blood in the tissue region has a second volume, the first light being substantially in a red light range and the second light being substantially in an infrared light range; detecting a red light signal and an infrared light signal, the red and infrared signals having at least first and second frequencies; computing a first ratio of the red and infrared signals at the first frequency; computing a second ratio of the red and infrared signals at the second frequency; comparing the first and second ratios to determine a first blood constituent.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF PREFERRED EMBODIMENTS

Figure 1:
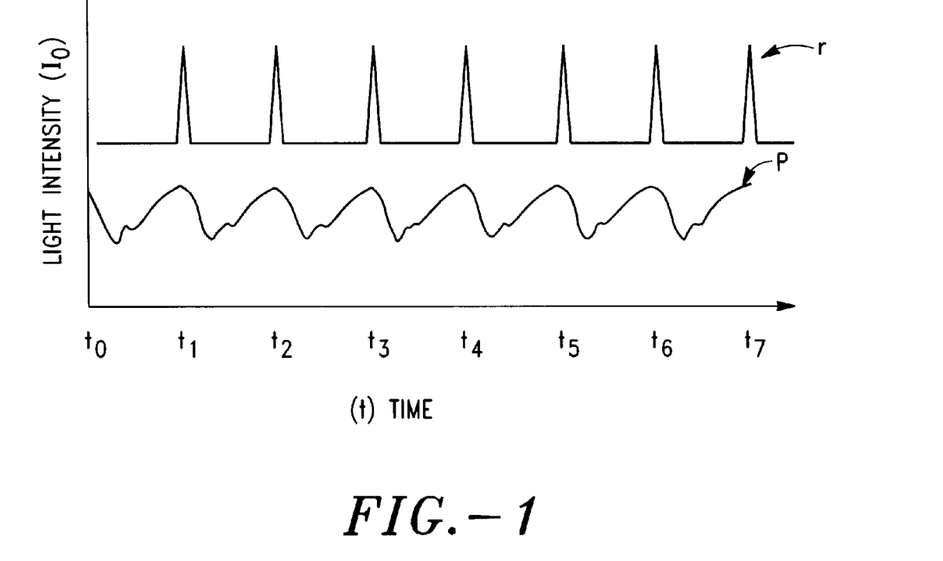
FIG. 1 is a graphical illustration of an r-wave portion of an electrocardiogram waveform and the related plethysmographic waveform.

Referring first to FIG. 1, there is shown a graphical illustration of an "r-wave" portion of an electrocardiogram (ECG) waveform (designated "r") and the related plethysmographic waveform (designated "p"). As will be appreciated by one having ordinary skill in the art, the ECG waveform comprises a complex waveform having several components that correspond to electrical heart activity. The QRS component relates to ventricular heart contraction.

The r-wave portion of the QRS component is typically the steepest wave therein, having the largest amplitude and slope, and may be used for indicating the onset of cardiovascular activity. The arterial blood pulse flows mechanically and its appearance in any part of the body typically follows the R wave of the electrical heart activity (i.e., r-wave event, designated $r_1$, $r_2$, $r_3$, etc. in FIG. 2) by a determinable period of time that remains essentially constant for a given patient. See, e.g., Goodlin et al., *Systolic Time Intervals in the Fetus and Neonate*, Obstetrics and Gynecology, Vol. 39, No. 2, (February 1972) and U.S. Pat. No. 3,734,086.

Correlating the occurrence of cardiovascular activity with the detection of arterial pulses typically occurs by measuring an ECG signal, detecting the occurrence of the r-wave portion of the ECG signal, determining the time delay by which an optical pulse in the detected optical signal follows the r-wave, and using the determined time delay between an r-wave and the following optical pulse to evaluate the waveform.

Figure 2:
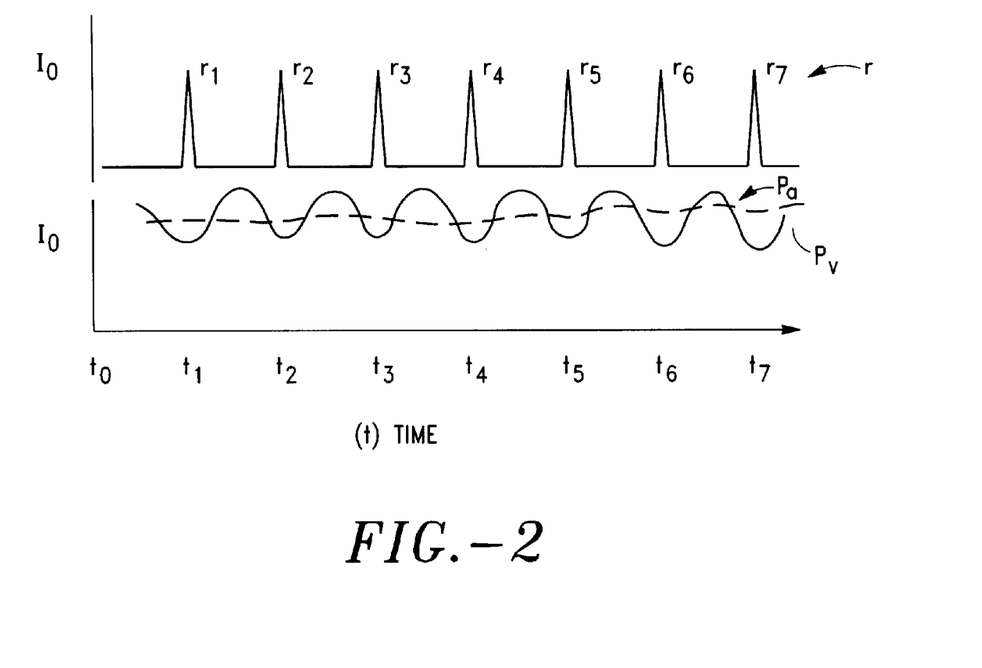
FIG. 2 is a graphical illustration of an r-wave portion of an electrocardiogram waveform and the related arterial blood pulse.

Referring now to FIG. 2, there is shown a graphical illustration of the arterial blood pressure (designated "$P_a$") which is similarly follows the r-wave event by a determinable period of time. The venous blood pressure (designated "$P_v$"), in the absence of extraneous forces or events (e.g., restricting venous blood flow), is typically relatively constant.

Figure 3:
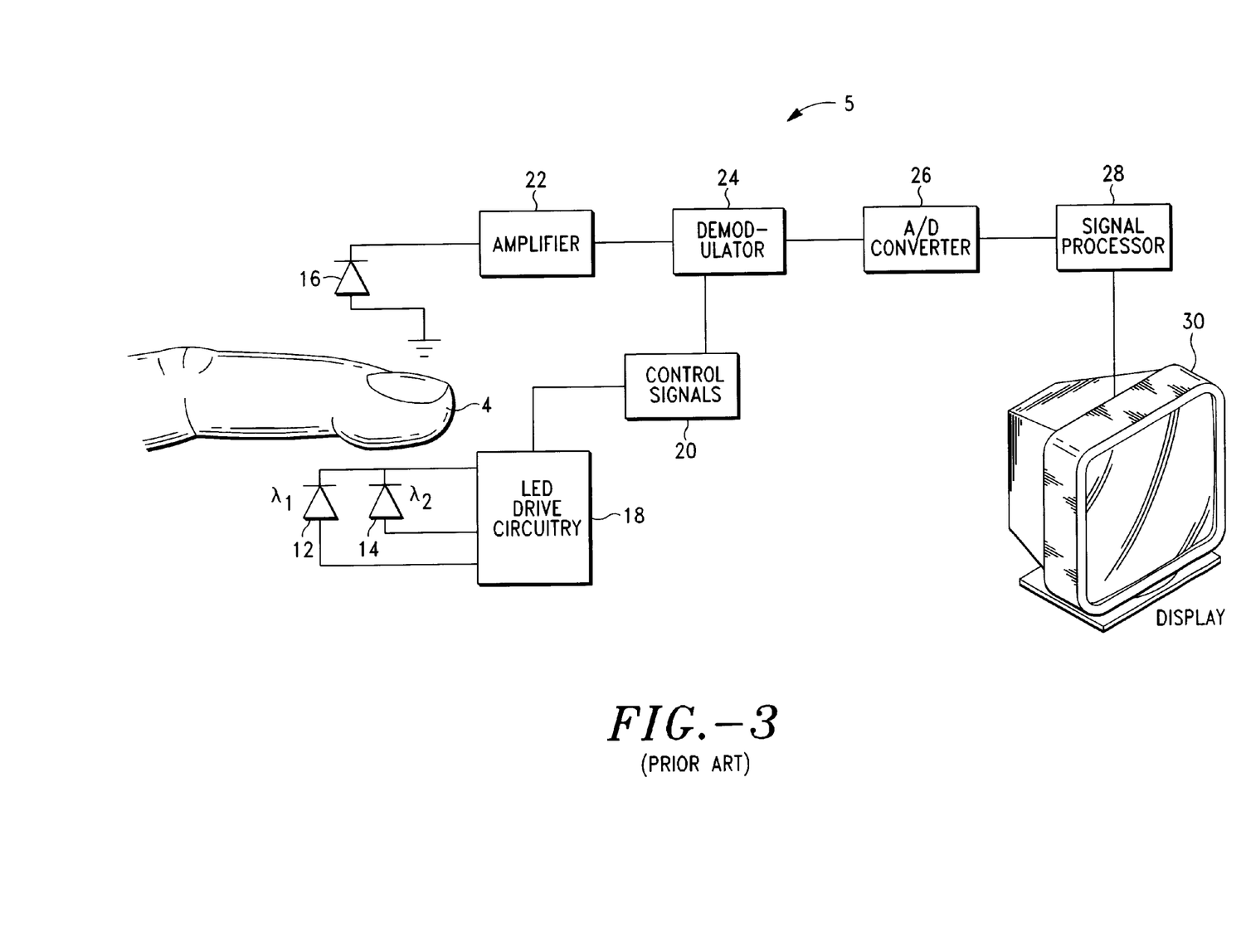
FIG. 3 is a schematic illustration of a prior art pulse oximeter apparatus.

Referring now to FIG. 3, there is shown a schematic illustration of one embodiment of a pulse oximeter apparatus 5 that can be employed within the scope of the invention. As discussed above, conventional pulse oximetry methods and apparatus typically employ two lights; a first light having a discrete frequency in the range of ~650–670 nanometers in the red range and a second light having a discrete frequency in the range of ~800–1000 nanometers.

The lights are typically directed through a finger 4 via emitters 12, 14 and detected by a photo detector 16. Emitters 12 and 14 are driven by drive circuitry 18, which is in turn governed by control signal circuitry 20. Detector 16 is in communication with amplifier 22.

The photo detector 16 provides an output signal $S_1$ that is transmitted to an amplifier 22. The amplified signal $S_1$ from amplifier 22 is then transmitted to demodulator 24, which is also synched to control signal circuitry 20. As will be appreciated by one having skill in the art, the output signal from the demodulator 24 would be a time multiplexed signal comprising (i) a background signal, (ii) the red light range signal and (iii) the infrared light range signal.

The demodulator 24, which is employed in most pulse oximeter systems, removes any common mode signals present and splits the time multiplexed signal ($S_1$) into two (2) channels, one representing the red voltage (or optical) signals (designated $S_3$) and the other representing the infrared voltage (or optical) signals (designated $S_4$).

As illustrated in FIG. 3, the signal from the demodulator 24 is transmitted to analog-digital converter 26. The desired computations are performed on the output from the converter 26 by signal processor 28 and the results transmitted to display 30.

Further details of the conventional pulse oximeter components, and related functions, are set forth in U.S. Pat. No. 4,934,372, which is incorporated by reference herein.

Figure 4:
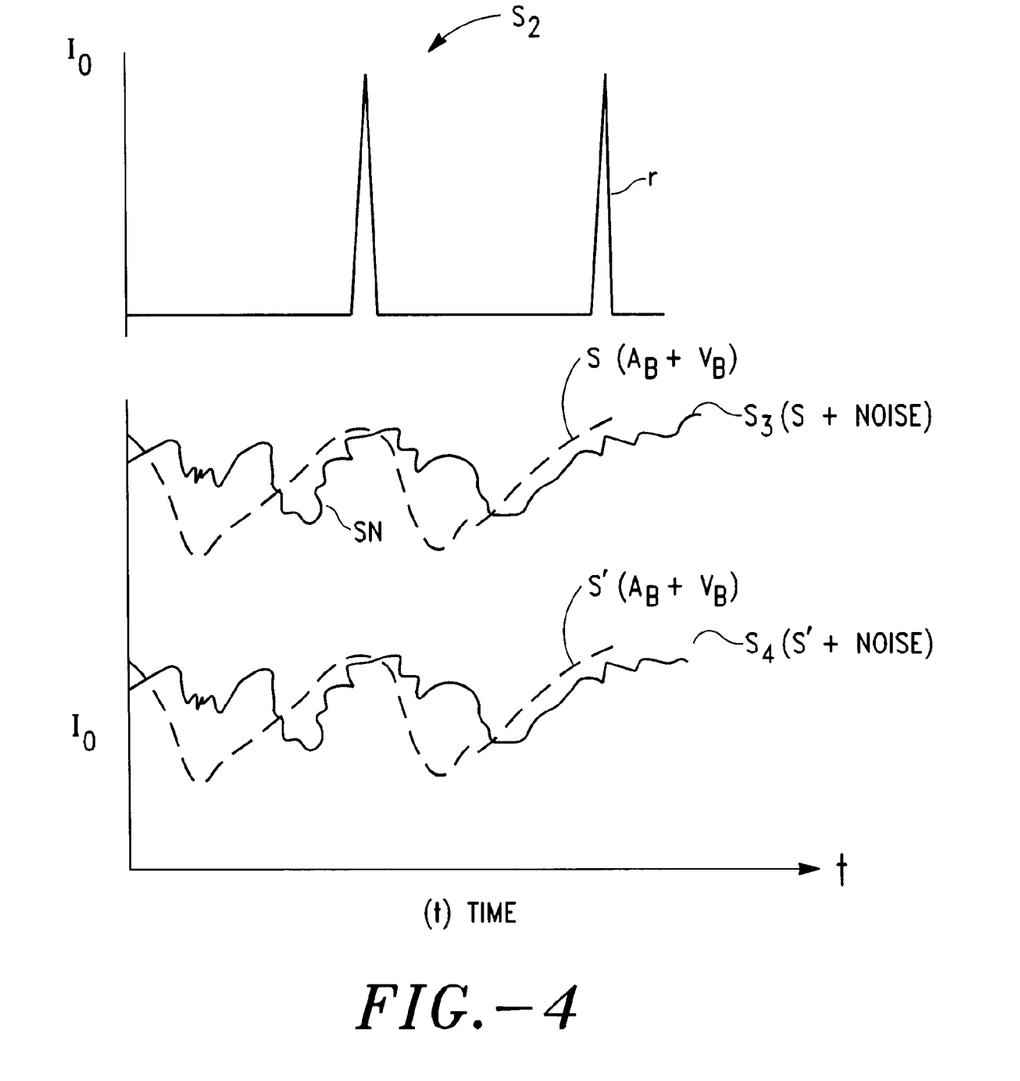
FIGS. 4 and 5 are graphical illustrations of red and infrared optical signals.

Referring now to FIG. 4, the red signal $S_3$ includes motion artifacts or noise and the base red signal S, which comprises arterial blood ($A_B$) and venous blood ($V_B$) components. The infrared signal $S_4$ similarly includes noise and the base infrared signal S.

Figure 5:
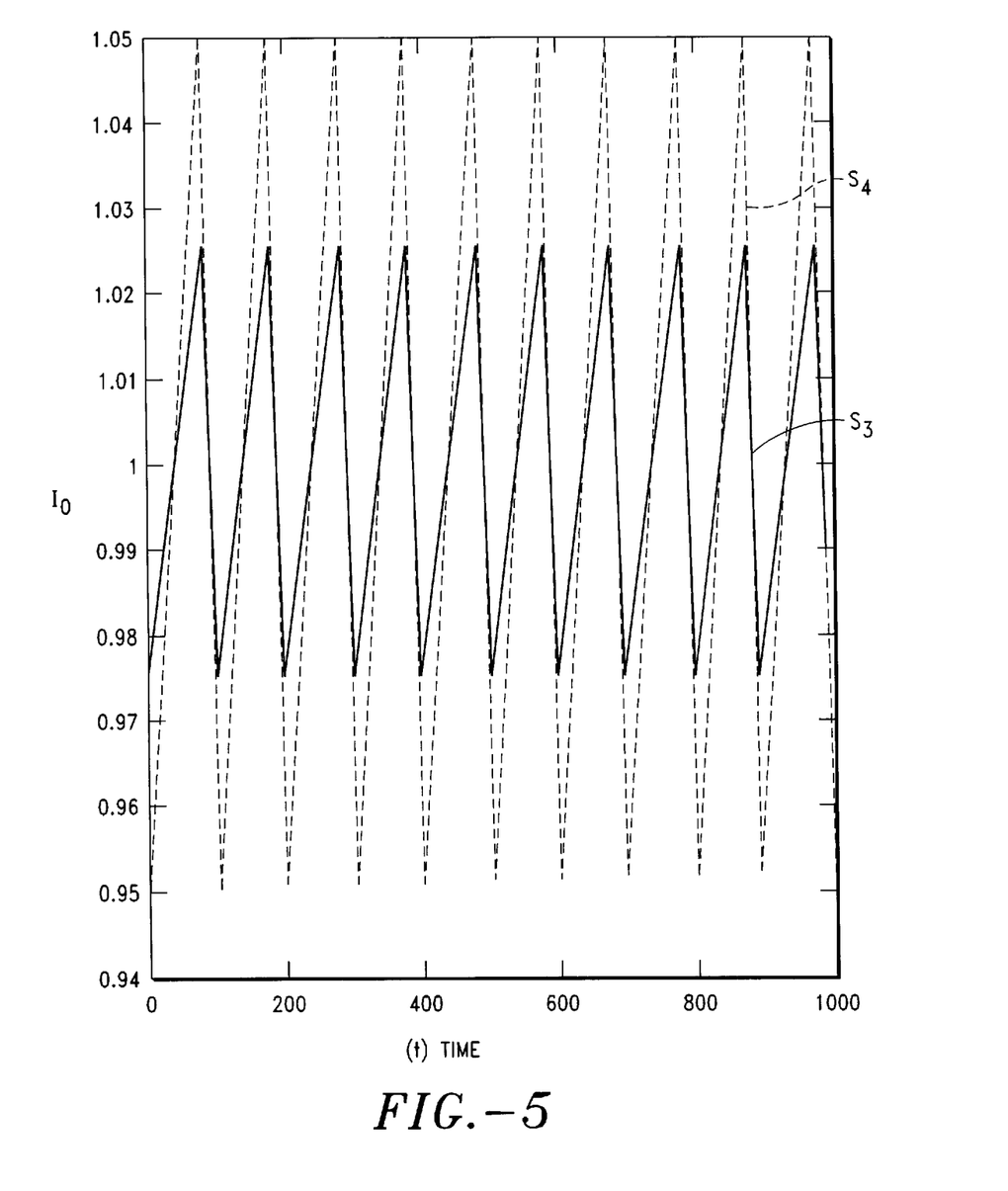

It should be noted that if the pulse oximeter apparatus 5 is designed correctly, such that the red and the infrared light pass through substantially the same tissue, the pulses in the plethysmographic waveform in the red channel, i.e., red voltage signal(s) $S_3$, will be shaped identically to those in the infrared channel, i.e., infrared voltage signal(s) $S_4$. Only their size and the slowly-varying voltage on which they sit will be different. (see FIG. 5)

Figure 6A:
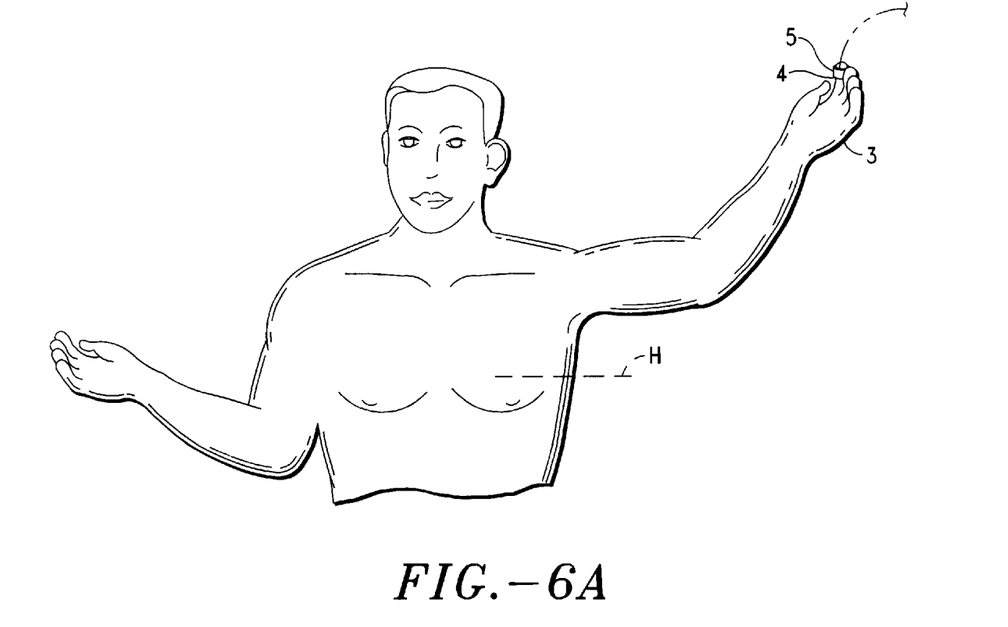
FIGS. 6A and 6B are schematic illustrations of a test subject showing the subject's positions during a test sequence according to the invention.
Figure 6B:
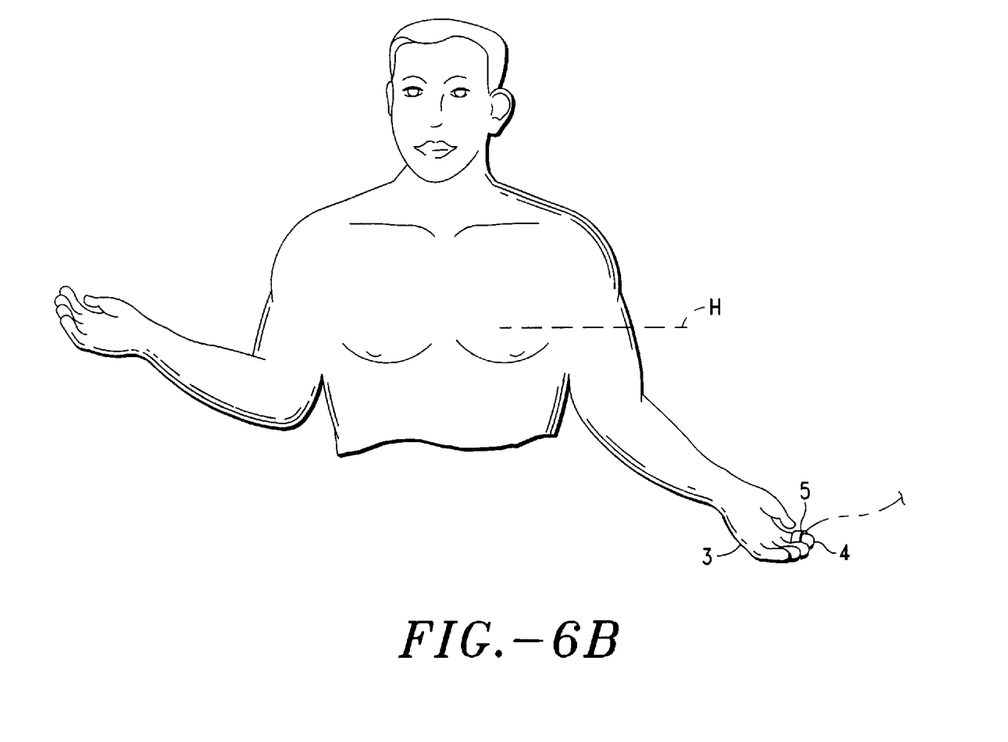

According to the invention, the venous blood component $V_B$ can be distinguished from the arterial blood component $V_A$ in the following manner: Referring to FIGS. 6A and 6B, in a first embodiment of the invention, the pulse oximeter 5 is operatively connected to a patient's finger 4. The patient's hand 3 (and, hence, finger 4) is then raised and held in a first position above the heart level (designated H) until substantially all of the venous (i.e., non-pulsating) blood is dissipated from or flows out of the finger 4. In a preferred embodiment, the hand 3 is held in the raised position for a first time period greater than 3 sec., more preferably, in the range of approximately 4.0 to 6.0 sec. During this first period of time, the red and infrared optical (or oximetry) signals are obtained.

The patient's hand 3 is then lowered to a second position below the heart level (H) for a substantially equal time period (see FIG. 6B). During this second period of time, the red and infrared optical (or oximetry) signals are also obtained.

Figure 7:
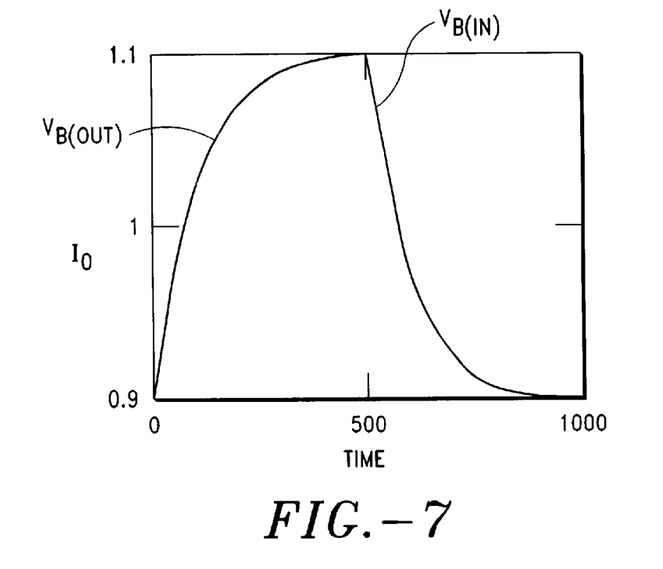
FIG. 7 is a graphical illustration of venous blood flow during a test sequence according to the invention.

Referring now to FIG. 7, there is shown a graphical illustration of the venous blood flow during the above described test cycle. As illustrated in FIG. 7, when the finger 4 is in the second position, i.e., below the heart level (H), venous blood flows into the finger 4, designated $V_{B(in)}$. When the finger is raised to the second position, venus blood dissipates from the finger 4, designated $V_{B(out)}$.

Figure 8:
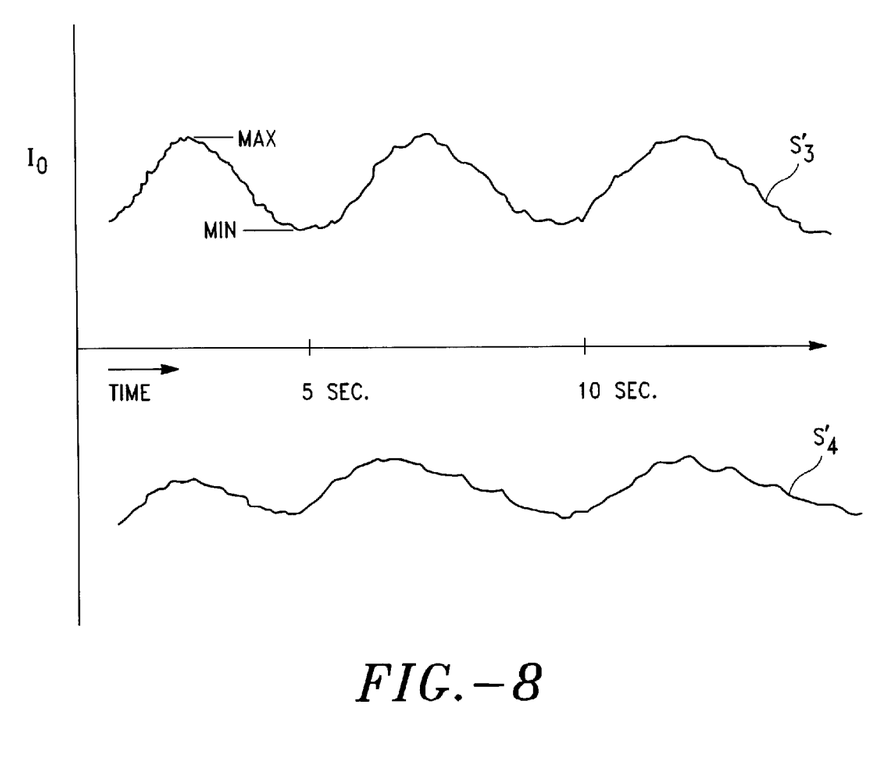
FIG. 8 is a further graphical illustration of red and infrared optical signals according to the invention.

After the oximetry signals are acquired, the ratios of the low frequency (i.e., 0.08 to 0.12 Hz) and high frequency (i.e., 0.8–1.2 Hz) signals of $S_3'$ (red) and $S_4'$ (infrared) are then computed and compared (see FIG. 8). According to the invention, the ratio of the extended time period (e.g., 10 sec) reflects the venous blood component ($V_B$).

Indeed, as will be appreciated by one having ordinary skill in the art, the ratio of the extended time period can only be attributed to the venous blood component ($V_B$), since a period of 10 sec. could not be attributed to the heart rate.

The following is an illustrative example: An oximeter sensor arrangement is coupled to a finger on patients A's left hand. The hand is raised over patient A's head and held for 4 sec. The hand is then lowered to Patient's A's side and held for 4 sec.

Figure 9:
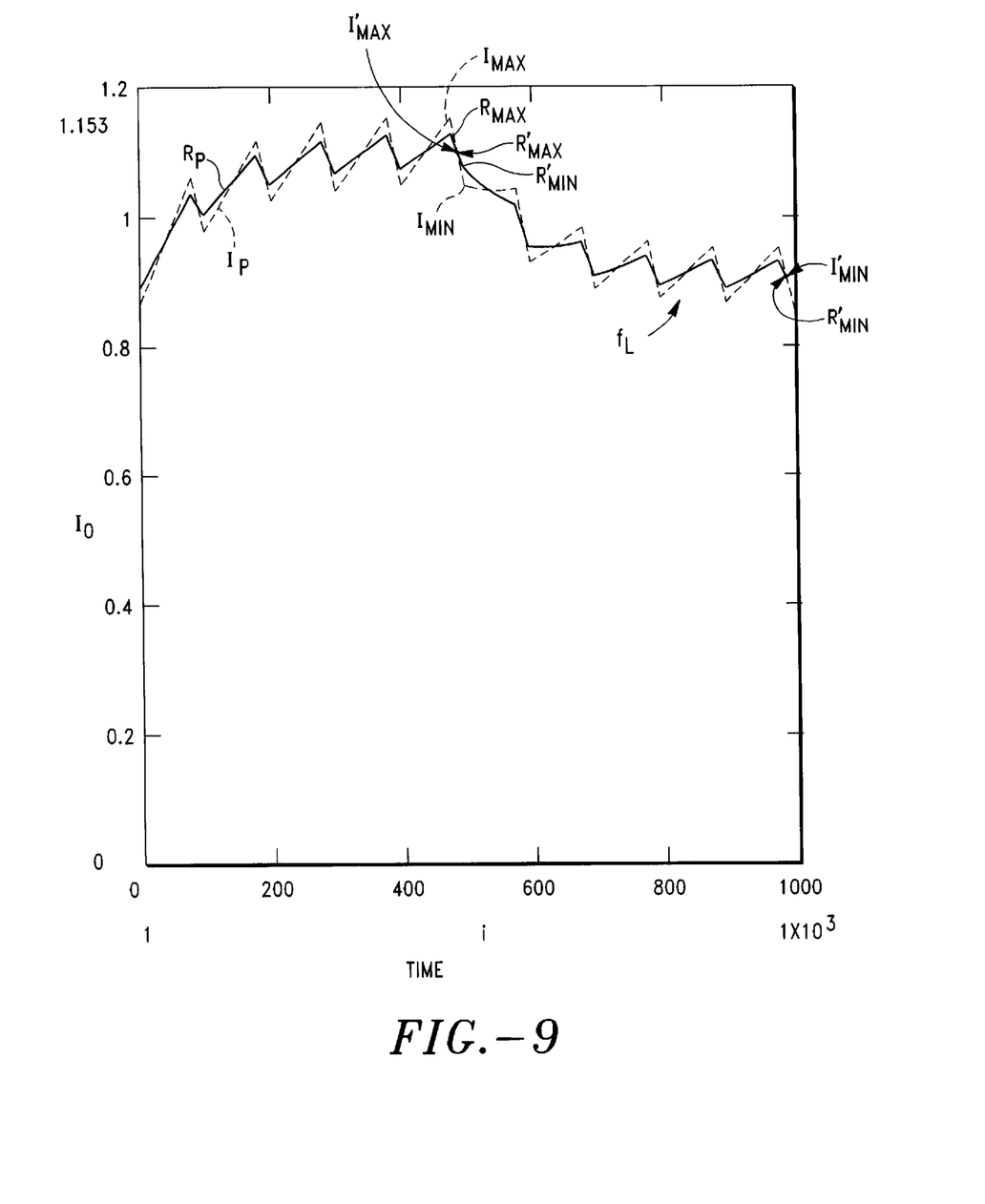
FIG. 9 is graphical illustration of red and infrared optical signals acquired during a test sequence according to the invention.

Referring now to FIG. 9, there is shown a representative modulation of red R and infrared I light for Patient A when both the venous concentration and arterial concentration are varying with time. As illustrated in FIG. 9, the arterial blood concentration is varying at approximately 1 cycle/sec. and the venous blood concentration is varying at approximately 1 cycle/10 sec.

As will be appreciated by one having ordinary skill in the art, the 1 cycle/sec. variation is due to the periodic changes in blood pressure attendant with each heart beat. The 1 cycle/10 sec. variation corresponds to the raising and lowering of the hand 3 above and below the heart level H within a 10.0 sec. period.

As illustrated in FIG. 9, the 1 cycle/sec. modulation has different amplitudes for red R and infrared I signals (i.e., "saw-tooth" shaped waveform). The 1 cycle/10 sec. modulation has the same amplitude for the red R and infrared I signals.

According to the invention, the same ratio variations at low frequencies, designated generally $f_1$, is indicative of a venous blood saturation of approximately 81%. The 2:1 amplitude variations (of the infrared to red signals) at 1 cycle/sec. is indicative of an arterial blood saturation of approximately 97%.

The following data can thus be acquired from FIG. 9:
High Frequency Components
$I_{max}$=infrared maximum intensity (pulsatile)=~1.155
$R_{max}$=red maximum intensity (pulsatile)=~1.1275
$I_{min}$=infrared minimum intensity (pulsatile)=~1.05
$R_{min}$=red minimum intensity (pulsatile)=~1.0725
$R'_{max}$=red average maximum intensity (venous)=~1.10
$I'_{max}$=infrared average maximum intensity (venous)= ~1.10
Low Frequency Components
$R'_{min}$=red average minimum intensity (venous)=~0.9
$I'_{min}$=infrared average minimum intensity (venous)=~0.9

According to the invention, the arterial and venous blood components of the noted oximetry signals can be determined as follows:

$$V_a=\ln R_{max}/R_{min}/\ln I_{max}/I_{min}=0.52 \qquad \text{Eq. 1}$$

$$V_b=\ln R'_{max}/R'_{min}/\ln I'_{max}/I'_{min}=1.0 \qquad \text{Eq. 2}$$

The arterial blood component, $V_a$, would thus correspond to a saturation level of approx. 97%. The venous blood component, $V_b$, would thus correspond to a saturation level of approx. 80%.

In an additional embodiment of the invention, the red (R) and infrared (I) signals are achieved by sequentially blocking and releasing the blood flow to the tissue (e.g., finger) coupled to the pulse oximeter. Various means may be employed to block and release the blood flow, such as a cuff disposed on the finger. (see, e.g., U.S. Pat. No. 4,883,055)

As will be appreciated by one having ordinary skill in the art, the noted method can be employed with virtually all pulse oximeter methods and apparatus to enhance the accuracy of the output data (i.e., plethysmographic waveform). The method can similarly be employed in the method and apparatus described in Co-pending application Ser. No. 09/815,827, filed Mar. 23, 2001, entitled "Method and Apparatus for Determining Physiological Characteristics."

The method of the invention is also particularly advantageous when employed in any device where venous saturation could interfere with the accuracy of the output data.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for determining blood constituents of a patient, said patient having a tissue region, said tissue region including venous and arterial blood, comprising;

coupling an oximeter sensor arrangement to said tissue region of said patient; passing first and second lights through said patient's tissue region while said venous blood in said tissue region has a first volume for a first period of time and said venous blood in said tissue region has a second volume for a second period of time, said first light being substantially in a red light range and said second light being substantially in an infrared light range;

detecting light absorbed by said tissue region and providing a first signal corresponding to said absorbed light;

processing said first signal to provide a second signal corresponding to a red light signal component and a third signal corresponding to an infrared light signal component, each of said second and third signals having at least first and second frequencies, wherein said first frequency comprises approximately the reciprocal of the sum of said first and second periods;

computing a first ratio of said second and third signals at said first frequency;

computing a second ratio of said second and third signals at said second frequency;

comparing said first and second ratios to determine a first blood constituent.

2. The method of claim 1, wherein said first light is in the range of approximately 650–670 nm.

3. The method of claim 1, wherein said second light is in the range of approximately 800–1000 nm.

4. The method of claim 1, wherein said first volume of said venous blood is substantially less than said second volume of said venous blood.

5. The method of claim 1, wherein said first and second periods of time are in the range of approximately 4–6 sec.

6. The method of claim 5, wherein said first and second periods of time are substantially equal.

7. The method of claim 1, wherein said first frequency is in the range of approximately 0.08–0.12 Hz.

8. The method of claim 1, wherein said second frequency is in the range of approximately 0.8–1.2 Hz.

9. The method of claim 1, wherein said first blood constituent comprises a venous blood component.

10. A method for determining blood constituents of a patient, comprising;

passing first and second lights through said patient's tissue while said tissue is in a first position for a first period of time and in a second period for a second period of time, said first position being above the patient's heart level and said second position being below said patient's heart region, said first light being substantially in a red light range and said second light being substantially in an infrared light range;

detecting light absorbed by said tissue and providing a first signal corresponding to said absorbed light;

processing said first signal to provide a second signal corresponding to a red light signal component and a third signal corresponding to an infrared light signal component, each of said second and third signals having at least first and second frequencies, wherein said first frequency comprises approximately the reciprocal of the sum of said first and second periods;

computing a first ratio of said second and third signals at said first frequency;

computing a second ratio of said second and third signals at said second frequency;

comparing said first and second ratios to determine a first blood constituent.

11. The method of claim 10, wherein said first light is in the range of approximately 650–670 nm.

12. The method of claim 10, wherein said second light is in the range of approximately 800–1000 nm.

13. The method of claim 10, wherein said first period of time is in the range of approximately 4–6 sec.

14. The method of claim 10, wherein said second period of time is in the range of approximately 4–6 sec.

15. The method of claim 14, wherein said first and second periods of time are substantially equal.

16. The method of claim 10, wherein said first frequency is in the range of approximately 0.08–0.12 Hz.

17. The method of claim 10, wherein said second frequency is in the range of approximately 0.8–1.2 Hz.

18. The method of claim 10, wherein said first blood constituent comprises a venous blood component.

19. A method for determining blood constituents of a patient, comprising;

passing first and second lights through said patient's tissue while said tissue is in a first position for a first period of time and in a second position for a second period of time, said first position being above the patient's heart level and said second position being below said patient's heart region, said first light being substantially in a red light range and said second light being substantially in an infrared light;

detecting a red light signal and an infrared light signal, said red and infrared signals having at least first and second frequencies, wherein said first frequency comprises approximately the reciprocal of the sum of said first and second periods;

computing a first ratio of said red and infrared signals at said first frequency;

computing a second ratio of said red and infrared signals at said second frequency;

comparing said first and second ratios to determine a first blood constituent.

20. The method of claim 19, wherein said first light is in the range of approximately 650–670 nm.

21. The method of claim 19, wherein said second light is in the range of approximately 800–100 nm.

22. The method of claim 19, wherein said first period of time is in the range of approximately 4–6 sec.

23. The method of claim 19, wherein said second period of time is in the range of approximately 4–6 sec.

24. The method of claim 23, wherein said first and second periods of time are substantially equal.

25. The method of claim 19, wherein said first frequency is in the range of approximately 0.08–0.12 Hz.

26. The method of claim 19, wherein said second frequency is in the range of approximately 0.8–1.2 Hz.

27. The method of claim 19, wherein said first blood constituent comprises a venous blood component.

* * * * *